US012740696B2

(12) United States Patent
Tsimerman

(10) Patent No.: US 12,740,696 B2
(45) Date of Patent: Sep. 22, 2026

(54) DENTAL MIRROR TOOL

(71) Applicant: Daniel Tsimerman, Vancouver (CA)

(72) Inventor: Daniel Tsimerman, Vancouver (CA)

( * ) Notice: Subject to any disclaimer, the term of this patent is extended or adjusted under 35 U.S.C. 154(b) by 281 days.

(21) Appl. No.: 18/300,135

(22) Filed: Apr. 13, 2023

(65) Prior Publication Data

US 2024/0341582 A1 Oct. 17, 2024

(51) Int. Cl.
*A61B 1/247* (2006.01)
*A61B 1/00* (2006.01)

(52) U.S. Cl.
CPC .......... *A61B 1/247* (2013.01); *A61B 1/00039* (2013.01); *A61B 1/00183* (2013.01)

(58) Field of Classification Search
None
See application file for complete search history.

(56) References Cited

U.S. PATENT DOCUMENTS 2,948,912 A * 8/1960 Wisdom ................. A61B 1/253 15/250.1
3,829,199 A 8/1974 Brown
4,408,991 A * 10/1983 Engel ..................... A61B 1/253 433/30
4,511,329 A * 4/1985 Diamond ............... A61C 17/10 433/160
4,713,002 A 12/1987 Berke
5,139,420 A 8/1992 Walker
5,654,824 A * 8/1997 Tarr ........................ A61B 1/126 359/872
6,142,777 A 11/2000 Winston et al.
6,254,386 B1 7/2001 Ohmes
6,474,989 B1 * 11/2002 Berk ...................... A61B 1/247 433/30
6,575,744 B1 * 6/2003 Oshida ................... A61B 1/127 359/872
7,021,798 B2 4/2006 Tsimerman et al.
8,142,352 B2 3/2012 Vivenzio et al.
10,206,563 B2 2/2019 Carron
11,278,198 B1 3/2022 Elazar et al.
(Continued)

FOREIGN PATENT DOCUMENTS

CN 1887214 A * 1/2007 ............. A61B 1/247
KR 100902362 B1 * 6/2009 ............. A61B 1/247
(Continued)

*Primary Examiner* — Heidi M Eide
(74) *Attorney, Agent, or Firm* — Brion Raffoul

(57) ABSTRACT

A self-cleaning dental mirror tool. The dental mirror tool includes a handle portion, a neck portion, a power pack, and a head portion. The handle portion holds the power pack. The power pack is self-contained within a housing. This power pack comprises a motor, a control switch, and one or more batteries. The power pack is removable from the handle portion. An adaptor is affixed to the end of the drive shaft of the motor. The adaptor engages a pinion having a circular bevel gear. The circular bevel gear engages an annular gearing ring on a rotor assembly having a rotor shaft and a disc to which a mirror is affixed. The mirror may be in the form of a detachable sticker with a reflective surface. In use, the mirror rotates at high speed. This high-speed rotation expels water and debris from the surface of the mirror.

16 Claims, 6 Drawing Sheets

(56) References Cited

U.S. PATENT DOCUMENTS

| | | | | |
|---|---|---|---|---|
| 2002/0157198 | A1* | 10/2002 | Biro | A61C 17/22 15/28 |
| 2004/0229187 | A1* | 11/2004 | Bretscher | G02B 5/3083 433/30 |
| 2010/0261132 | A1 | 10/2010 | Widen | |
| 2012/0021373 | A1 | 1/2012 | Moreno | |
| 2013/0289465 | A1* | 10/2013 | Hohnbaum | A61F 13/024 602/57 |
| 2016/0278625 | A1 | 9/2016 | Solomon | |
| 2016/0302655 | A1* | 10/2016 | Carron | A61B 1/00066 |
| 2017/0202446 | A1 | 7/2017 | Watson et al. | |
| 2018/0168441 | A1* | 6/2018 | Tavor | A61C 17/08 |
| 2020/0337545 | A1* | 10/2020 | Berkovic | A61B 1/00042 |
| 2020/0341169 | A1 | 10/2020 | Nakamatsu | |
| 2021/0298885 | A1* | 9/2021 | Barrilleaux | A61C 19/08 |
| 2023/0122799 | A1* | 4/2023 | Al Safer | A61B 1/253 433/30 |

FOREIGN PATENT DOCUMENTS

| | | | | |
|---|---|---|---|---|
| KR | 1887214 | B1 * | 8/2018 | B65H 3/22 |
| WO | WO-9958045 | A1 * | 11/1999 | A61B 1/247 |
| WO | 2014140795 | A1 | 9/2016 | |

* cited by examiner

DENTAL MIRROR TOOL

TECHNICAL FIELD

The present invention relates to dental mirrors. More specifically, the present invention relates to reusable self-cleaning dental mirrors.

BACKGROUND

When performing dental procedures, a dentist's view of a patient's oral cavity is often obstructed. To allow a dentist a more complete view of the patient's oral cavity, the dentist will often use a dental mirror tool. The mirror on the tool allows the dentist to observe features that are otherwise concealed. The dental mirror is typically mounted on a handle and the plane of the mirror is at an angle to the handle.

Dental mirror tools are often used in conjunction with other dental instruments in the oral cavity. During dental procedures, there may be a flow of cooling liquid from cutting handpieces or scalar handpieces. Other debris, such as cleaning grit or material removed from the tooth, may also land on the dental mirror. This liquid and/or debris on the mirror will impair the dentist's ability to see the targeted area of the oral cavity. Accordingly, the dentist or dental assistant is forced to frequently clean the mirror to remove this liquid and debris, thus interrupting the procedure. These interruptions correspondingly lengthen the procedure, causing discomfort to the patient and reducing the efficiency of the dentist.

There are numerous methods by which a dentist can remove the liquid and debris. Often, the dentist will continuously manually wipe off the mirror with gauze. Alternatively, the dental assistant may blow air on the dentist's mirror. Air blowing is not effective in all parts of the mouth because the confined spaces of the oral cavity limit the relative angles of the air jet and the mirror.

To overcome this problem, self-cleaning mirror tools have been created. However, each self-cleaning mechanism has its disadvantages.

Such self-cleaning mechanisms may be pneumatic. Pneumatic mechanisms can use suction or drive rotation of the mirror. However, such devices can be cumbersome due to the pneumatic hoses used and are of limited efficacy.

Self-cleaning mirrors may also use an electrically driven motor to rapidly rotate the mirror. U.S. Pat. No. 7,021,798, which is incorporated herein by reference, discloses a self-cleaning dental mirror tool that uses a rapidly rotating mirror to remove liquid and debris. The centrifugal force created by rapid rotation expels the liquid and debris from the mirror.

However, present rotating dental mirror tools can have numerous disadvantages. As reusable dental mirror tools must be autoclaved between patients, all components of the mirror must be resistant to high temperature, steam, and pressure unless they are removed from the device prior to autoclaving. Autoclavable electronic components are very expensive, discouraging the use of such a type of mirror. Further, contacting the mirror with another dental instrument while it rotates will cause a 360° scratch, thus obscuring the dentist's view. The mirror must then be replaced at considerable expense.

Additionally, a dentist requires multiple units of such autoclaved mirrors to have devices ready for each patient throughout the day.

Accordingly, there is a need for a dental mirror tool that is self-cleaning, economical, and readily reusable.

SUMMARY

The present invention provides a dental mirror tool that is self-cleaning. The dental mirror tool includes a handle portion, a neck portion, a power pack, and a head portion. The handle portion holds the power pack. The power pack is self-contained within a housing. This power pack comprises a motor, a control switch, and one or more batteries. The power pack is removable from the handle portion. An adaptor is affixed to the end of the drive shaft of the motor. The adaptor engages a pinion having a circular bevel gear. The circular bevel gear engages an annular gearing ring on a rotor assembly having a rotor shaft and a disc to which a mirror is affixed. The mirror may be in the form of a detachable sticker with a reflective surface. In use, the mirror rotates at high speed. This high-speed rotation expels water and debris from the surface of the mirror.

In a first aspect, this document discloses a dental mirror tool comprising: a handle portion; a power pack comprising: a motor having a drive shaft affixed to an adaptor; a control switch; and at least one battery, a neck portion; a head portion, said head portion comprising: a housing; a rotor assembly comprising: a rotor comprising a rotor shaft, an annular gearing ring, and a disc; and a retaining means; and a pinion comprising: a distal end having a circular bevel gear; a pinion shaft; and a proximal end having a receiving slot, wherein said distal end and said proximal end are on opposing ends of said pinion shaft; and a mirror, wherein said power pack is removably inserted in said handle portion; wherein when said power pack is inserted in said handle portion, said adaptor is received by said receiving slot; wherein said housing houses said rotor assembly and wherein said retaining means retains said rotor assembly within said housing, wherein said disc comprises a first side and a second side, wherein said rotor shaft projects from said second side such that said rotor shaft is perpendicular to said disc, wherein said circular bevel gear operatively engages said annular gearing ring, wherein said adaptor is received by said receiving slot to thereby operatively couple said motor to said disc, wherein said mirror is affixed to said first side, wherein said neck portion joins said handle portion to said head portion, and wherein when said motor operates, said drive shaft rotates to thereby rotate said rotor shaft to thereby cause said disc to rotate.

In a second aspect, this document discloses a dental mirror tool comprising: a handle portion, a neck portion, a power pack comprising a motor having a drive shaft affixed to an adaptor; a head portion, said head portion comprising: a housing; a rotor assembly comprising: a rotor comprising a rotor shaft, an annular gearing ring, and a disc; and a retaining means; and a pinion comprising: a circular bevel gear; and a pinion shaft; and a mirror, wherein said power pack is removably inserted in said handle portion; wherein when said power pack is inserted in said handle portion, said adaptor engages said pinion; wherein said housing houses said rotor assembly and wherein said retaining means retains said rotor assembly within said housing, wherein said disc comprises a first side and a second side, wherein said rotor shaft projects from said second side such that said rotor shaft is perpendicular to said disc, wherein said circular bevel gear operatively engages said annular gearing ring, wherein said mirror is affixed to said first side, wherein said neck portion joins said handle portion to said head portion, and wherein when said motor operates, said drive shaft rotates to thereby rotate said rotor shaft to thereby cause said disc to rotate.

BRIEF DESCRIPTION OF THE DRAWINGS

The present invention will now be described by reference to the following figures, in which identical reference numerals refer to identical elements and in which.

DETAILED DESCRIPTION

Figure 1:
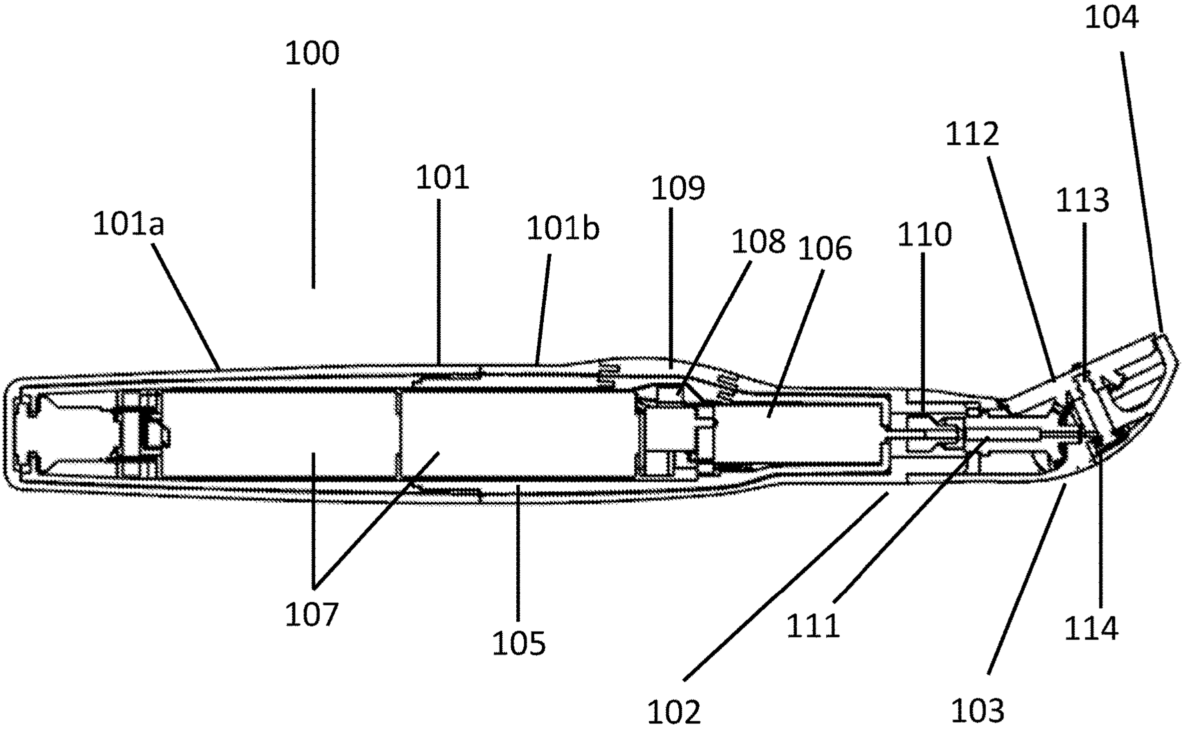
FIG. 1 is a cutaway view of an embodiment of the present invention.

Referring now to FIG. 1, an embodiment of the present invention is shown as a cutaway of the dental mirror tool 100. The body of the dental mirror tool 100 has a handle portion 101, a neck portion 102, and a head portion 103.

The handle portion 101 can be gripped or be otherwise manipulated by the dentist. The neck portion 102 connects the handle portion 101 to the head portion 103. The head portion 103 has a housing 104 in which the rotor assembly is mounted.

The handle portion 101 acts as an external, autoclavable sheathe for the removable power pack 105. The power pack 105 comprises a motor 106, one or more batteries 107, and a control switch 108. The one or more batteries 107 may be rechargeable or disposable. The control switch 108 operates to stop and start the motor 106. Preferably, the control switch 108 is a push button. In one embodiment, the control switch 108 is covered by an internal membrane on the power pack 105, which can be manipulated via an external membrane 109 on the handle portion 101. The internal membrane and external membrane 109 are aligned to allow a user to push the push button.

Figure 2:
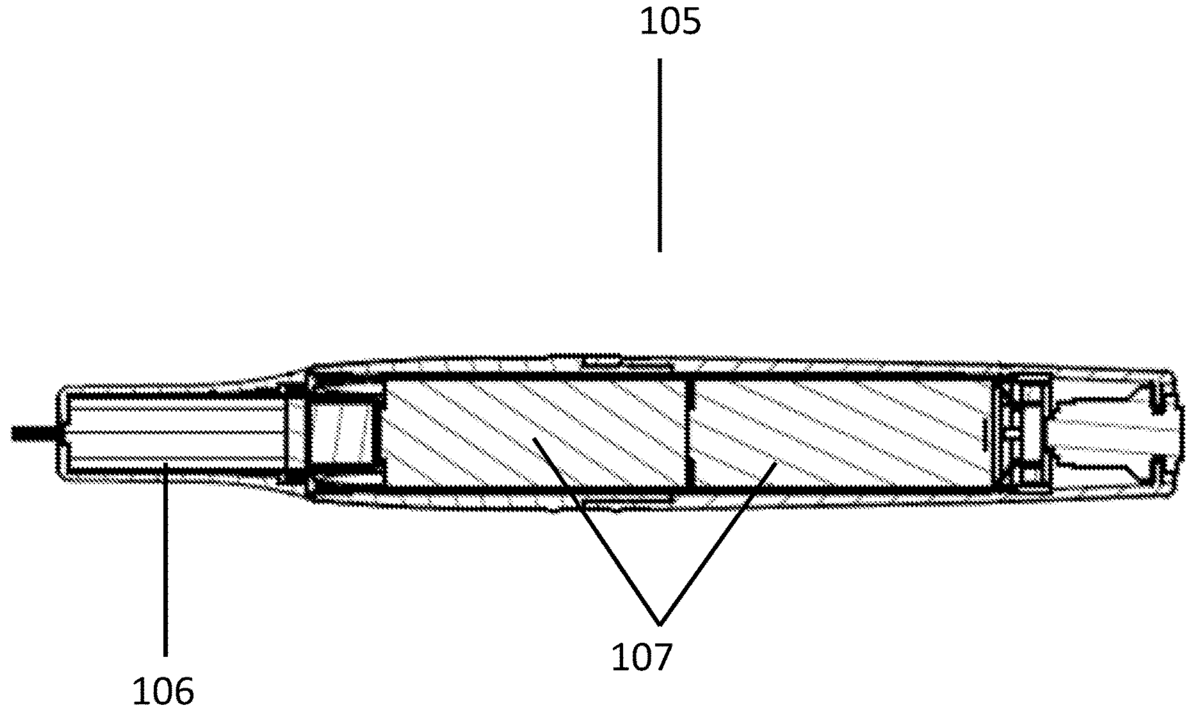
FIG. 2 is a cutaway view of an embodiment of a power pack according to the present invention.
Figure 3:
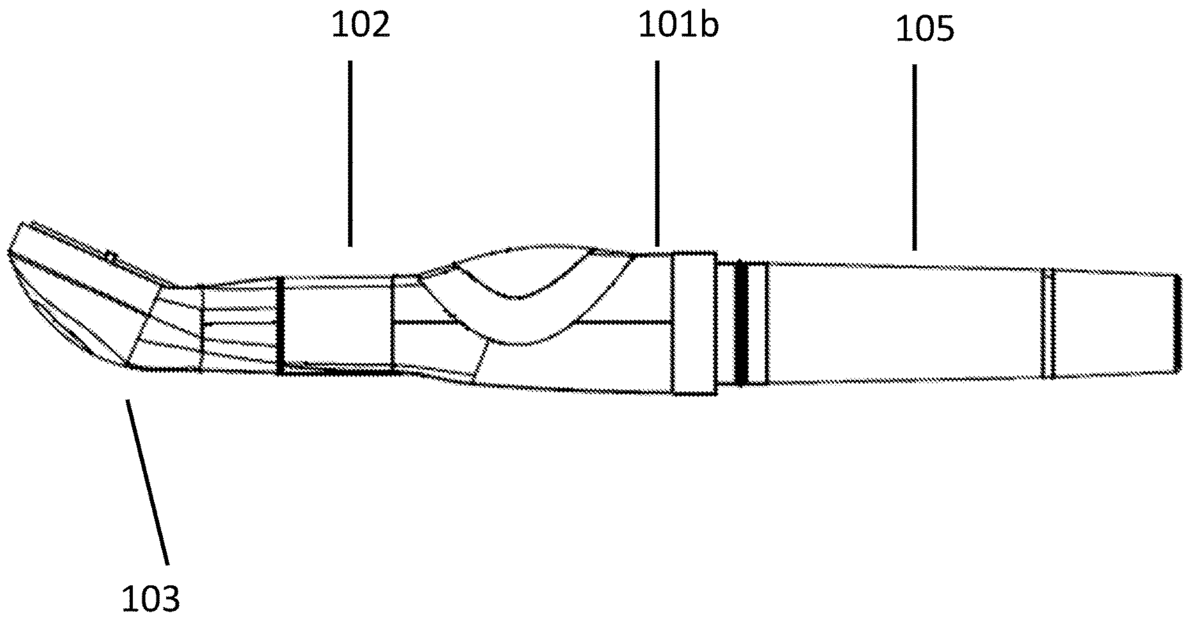
FIG. 3 is a view of an embodiment of a partial assembly of the present invention.

The handle portion 101 may be formed out of multiple sections that are detachable from each other. In a preferred embodiment, a rear section 101*a* of the handle portion 101 is detachable (e.g., through an annular snap joint) from a front section 101*b* of the handle portion 101. In such an embodiment, the front section 101*b* may be fused with the neck portion 102. Detachable sections allow for the removal of the power pack 105 shown in FIG. 2. Removal of the power pack 105, and thus the components within it, allows the rest of the dental mirror tool 100 to be autoclaved. Autoclaving is necessary for sterilization between patients. Advantageously, the motor 106 and the control switch 108 do not need to be heat, steam, and pressure-resistant, reducing complexity and cost. As shown in FIG. 3, the power pack 105 can be reinserted into the front section 101*b* after autoclaving.

Figure 4A:
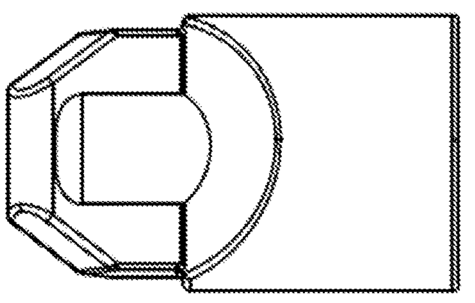
FIG. 4A is a side view of an adaptor forming part of the present invention.
Figure 4B:
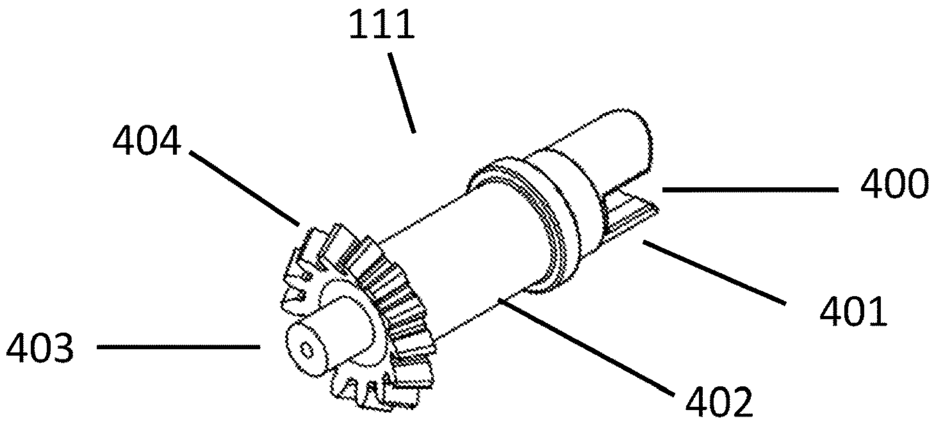
FIG. 4B is a perspective view of a pinion forming part of the present invention.
Figure 4C:
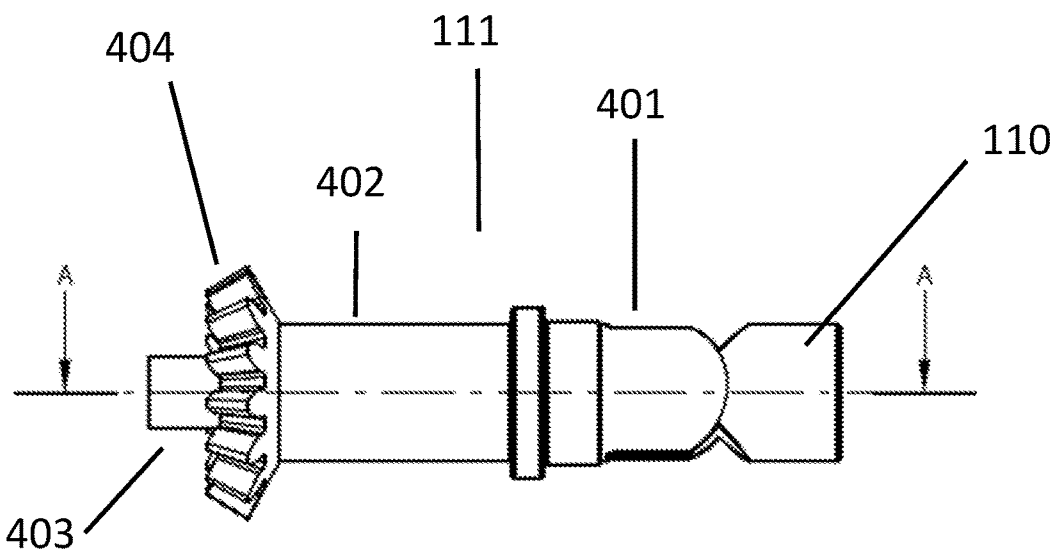
FIG. 4C is a side view of a pinion-adaptor assembly forming part of the present invention.

The motor 106 has a drive shaft that is affixed to an adaptor 110 shown in detail in FIG. 4A. The adaptor 110 is located in the neck portion 102 of the dental mirror tool 100. The adaptor 110 in turn is received by a receiving slot 400 in the proximal end 401 of the pinion 111 shown in FIG. 4B. The proximal end 401 of the pinion 111 is connected by the pinion shaft 402 to the distal end 403, which has a circular bevel gear 404. As shown in FIG. 4C, the adaptor 110 engages the receiving slot 400 of the pinion 111. The adaptor 110 and receiving slot 400 are correspondingly shaped to ensure that the adaptor 110 can securely engage the receiving slot 400 regardless of the position of the adaptor 110 when the power pack 105 is inserted into the handle portion 101. During such engagement, the motor 106 can drive the pinion 111 to rotate around an axis A-A.

Figure 5:
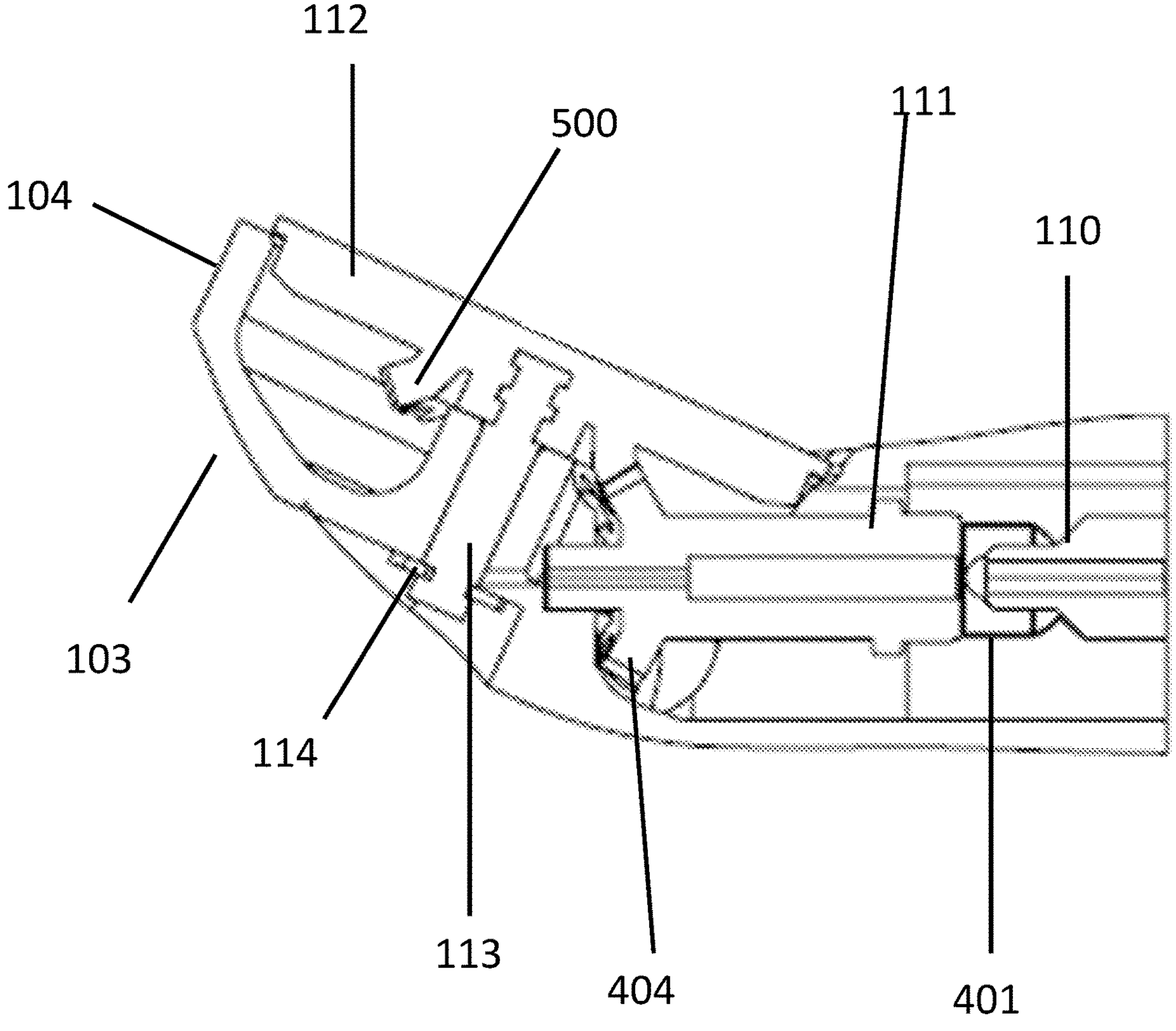
FIG. 5 is a cutaway view of a mirror head according to an embodiment of the present invention.

Referring now to FIG. 5, the head portion 103 of the dental mirror tool 100 is shown. The head portion 103 has a housing 104 in which a rotor assembly is mounted. The rotor assembly comprises a disc 112 from which a rotor shaft 113 projects into the housing 104. The rotor shaft 113 is retained in the housing 104 using any suitable retaining means. Preferably, a C-clip 114 retains the rotor shaft 113.

The rotor assembly further comprises an annular gearing ring 500. The annular gearing ring 500 is mounted to the disc 112 and surrounds the rotor shaft 113. It should be clear to a person of skill in the art that such an arrangement may include the fabrication of the gearing ring 500, the disc 112, and the rotor shaft 113 as a single piece. The circular bevel gear 404 engages the annular gearing ring 500, thus allowing the rotating pinion 111 to rotate the disc 112.

In operation, the motor 106 transmits rotational force through the drive shaft and the adaptor 110, which engages the receiving slot 400 of the pinion 111. The pinion shaft 402 operates to rotate the circular bevel gear 404, the teeth of which engage with the teeth of the annular gearing ring 500. As the annular gearing ring 500 rotates, the disc 112 and rotor shaft 113 also rotate. Preferably, the disc 112 rotates at a frequency of at least 8000 revolutions per minute. The high-speed rotation uses centrifugal force to remove any water or debris from the surface of the mirror.

Because the circular bevel gear 404 and the annular gearing ring 500 can engage on an angle, the disc 112 can also be angled relative to the pinion shaft 402, the neck portion 102, and the handle portion 101. Preferably, the disc 112 is angled at 100° to 170°. The angled disc 112 allows the dentist to view features of the oral cavity that may otherwise be obstructed.

Figure 6:
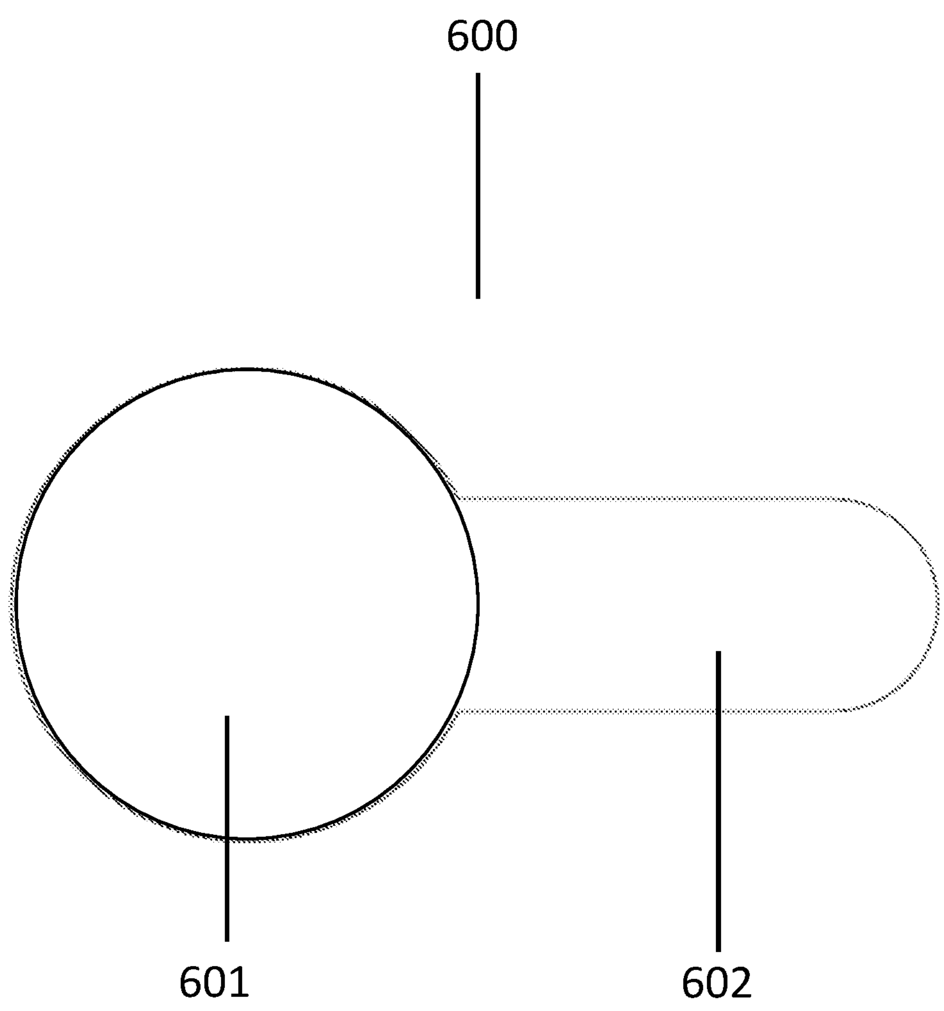
FIG. 6 is an embodiment of a detachable sticker according to the present invention.

Referring now to FIG. 6, a detachable sticker 600 is shown. The detachable sticker 600 comprises a mirror portion 601 with a reflective surface. The mirror portion 601 covers the disc 112 when the dental mirror tool 100 is in use.

The other surface of the detachable sticker 600 is coated with a removable adhesive, allowing the mirror portion 601 to adhere to the disc 112 with adequate strength to remain on the disc 112 during the procedure, yet flexible enough to be easily removed from the disc 112 following the procedure. Preferably, the adhesive releases under the high heat, steam, and pressure of an autoclave, allowing for the easy removal of the detachable sticker 600.

The reflective surface is reflective such that the mirror portion 601 reflects a view of the oral cavity towards the dentist when the dental mirror tool 100 is in use. Preferably, the reflective surface is formed of a thin film (e.g., polyethylene terephthalate) or sheet coated with a dielectric coating that has a substantially higher reflectivity than a standard rhodium-coated dental mirror. Preferably, the dielectric coating reflects at least 60%, or more preferably 95%, of visible light.

In a preferred embodiment, the detachable sticker 600 has a tongue 602. The tongue projects radially outwards from the edge of the mirror portion 601. The tongue 602 allows the user to grip the detachable sticker 600 without touching the reflective surface or the adhesive surface. The tongue 602 also helps the user to properly align the mirror portion 601 on the disc 112. The tongue 602 can be separated from the mirror portion 601 before the dental mirror tool 100 is used with a patient.

In a further preferred embodiment, the adhesive surface on the mirror portion 601 of the detachable sticker 600 is covered by a disposable protective layer. The reflective surface of the mirror portion 601 is covered by a disposable film layer that also forms the tongue 602. In such an embodiment, a user removes the disposable protective layer. The user then positions the mirror portion 601 to be centred over the disc 112 using the tongue 602. The user then affixes the mirror portion 601 to the disc 112 and removes the disposable film layer by lifting the tongue 602.

In another embodiment, the disc 112 has a notch that assists the dentist in the removal of the detachable sticker 600 from the disc 112. The notch provides the option of prying the detachable sticker 600 from the disc 112.

The expression 'at least one of X and Y', as used herein, means and should be construed as meaning 'X, or Y, or both X and Y'.

A person understanding this invention may now conceive of alternative structures and embodiments or variations of the above all of which are intended to fall within the scope of the invention as defined in the claims that follow.

I claim:

1. A dental mirror tool comprising:
a handle portion;
a power pack comprising:
a motor having a drive shaft affixed to an adaptor;
a control switch; and
at least one battery,
a neck portion;
a head portion, said head portion comprising:
a housing;
a rotor assembly comprising:
a rotor comprising a rotor shaft, an annular gearing ring, and a disc, wherein said rotor shaft, said annular gearing ring, and said disc are fabricated as a single piece, and wherein said annular gearing ring is integrated into an underside of said disc; and
a C-clip to retain said rotor shaft in said housing; and
a pinion comprising:
a pinion shaft having a distal end that is directly connected to a circular bevel gear; and
a proximal end having a receiving slot,
wherein said distal end and said proximal end are on opposing ends of said pinion shaft;
a mirror, and
a drive mechanism for rotating said disc, the drive mechanism consisting of:
said circular bevel gear having a first set of teeth; and said annular gearing ring having a second set of teeth, wherein said first set of teeth is meshed with said second set of teeth,
wherein when said drive shaft rotates as said motor operates, said pinion shaft rotates to thereby rotate said circular bevel gear and to thereby rotate said annular gearing ring and said disc by way of enmeshing between said first set of teeth and said second set of teeth,
wherein said power pack is removably inserted in said handle portion;
wherein when said power pack is inserted in said handle portion, said adaptor is received by said receiving slot;
wherein said housing houses said rotor assembly and wherein said C-clip retains said rotor assembly within said housing,
wherein said disc comprises a first side and a second side,
wherein said rotor shaft projects from said second side such that said rotor shaft is perpendicular to said disc,
wherein said adaptor is received by said receiving slot to thereby operatively couple said motor to said disc,
wherein said mirror is affixed to said first side,
wherein said neck portion joins said handle portion to said head portion,
wherein said mirror comprises a detachable sticker, said detachable sticker comprising:
a reflective surface; and
an adhesive surface,
wherein said reflective surface and said adhesive surface are on opposite sides of said sticker, and wherein said adhesive surface detachably affixes said mirror to said disc, such that said mirror is replaceable by a similar detachable sticker.

2. The dental mirror according to claim 1, wherein said handle portion comprises a plurality of sections, each section being detachable from at least one other section.

3. The dental mirror according to claim 2, wherein said plurality of sections comprises a front section and a rear section, wherein detaching said rear section from said front section allows the removal of said power pack.

4. The dental mirror tool according to claim 1, wherein removing said power pack from said handle portion renders said dental mirror tool suitable for autoclaving.

5. The dental mirror tool according to claim 1, wherein said control switch comprises a push button.

6. The dental mirror tool according to claim 5, wherein said handle portion further comprises an external membrane, wherein said power pack further comprises an internal membrane covering said push button, and wherein a user operates said push button by pushing said external membrane.

7. The dental mirror tool according to claim 1, wherein said circular bevel gear operatively engages said annular gearing ring at an angle such that the plane of said disc is at a 100° to 170° angle relative to a longitudinal axis of said pinion shaft.

8. The dental mirror tool according to claim 1, wherein said detachable sticker further comprises a removable tongue and wherein said tongue projects radially outwards from said detachable sticker.

9. The dental mirror tool according to claim 1, wherein said reflective surface reflects at least 60% of visible light.

10. The dental mirror tool according to claim 1, wherein said disc rotates at a frequency of at least 8000 revolutions per minute.

11. The dental mirror tool according to claim 1, wherein said disc comprises a notch.

12. A dental mirror tool comprising:
a handle portion,
a neck portion,
a power pack comprising a motor having a drive shaft affixed to an adaptor;
a head portion, said head portion comprising:
a housing;
a rotor assembly comprising:

a rotor comprising a rotor shaft, an annular gearing ring, and a disc, wherein said rotor shaft, said annular gearing ring, and said disc are fabricated as a single piece, and wherein said annular gearing ring is integrated into an underside of said disc; and a C-clip to retain said rotor shaft in said housing; and a pinion comprising:

a pinion shaft having a distal end that is directly connected to a circular bevel gear; and a mirror, and a drive mechanism for rotating said disc, the drive mechanism consisting of:

said circular bevel gear having a first set of teeth; and said annular gearing ring having a second set of teeth;

wherein said first set of teeth is meshed with said second set of teeth;

wherein when said drive shaft rotates as said motor operates, said pinion shaft rotates to thereby rotate said circular bevel gear and to thereby rotate said annular gearing ring and said disc by way of enmeshing between said first set of teeth and said second set of teeth, wherein said power pack is removably inserted in said handle portion;

wherein when said power pack is inserted in said handle portion, said adaptor engages said pinion;

wherein said housing houses said rotor assembly and wherein said C-clip retains said rotor assembly within said housing, wherein said disc comprises a first side and a second side, wherein said rotor shaft projects from said second side such that said rotor shaft is perpendicular to said disc, wherein said mirror is affixed to said first side, wherein said neck portion joins said handle portion to said head portion, wherein said mirror comprises a detachable sticker, said detachable sticker comprising:

a reflective surface; and an adhesive surface, wherein said reflective surface and said adhesive surface are on opposite sides of said sticker, and wherein said adhesive surface detachably affixes said mirror to said disc, such that said mirror is replaceable by a similar detachable sticker.

13. The dental mirror tool according to claim 12, wherein said circular bevel gear operatively engages said annular gearing ring at an angle such that the plane of said disc is at a 100° to 170° angle relative to a longitudinal axis of said pinion shaft.

14. The dental mirror tool according to claim 12, wherein said detachable sticker further comprises a removable tongue and wherein said tongue projects radially outwards from said detachable sticker.

15. The dental mirror tool according to claim 12, wherein said reflective surface reflects at least 60% of visible light.

16. The dental mirror tool according to claim 12, wherein said disc rotates at a frequency of at least 8000 revolutions per minute.

* * * * *